United States Patent
Besch et al.

(10) Patent No.: US 10,238,445 B2
(45) Date of Patent: Mar. 26, 2019

(54) DEVICE FOR THE FLUID-CONVEYING CONNECTION OF AT LEAST ONE APPLICATION PROBE WITH A SUPPLY TUBING SET, AND HANDLE FOR A SURGICAL INSTRUMENT

(75) Inventors: Hansjörg Besch, Gomaringen (DE); Markus Amann, Tubingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 1020 days.

(21) Appl. No.: 13/211,954

(22) Filed: Aug. 17, 2011

(65) Prior Publication Data

US 2012/0046655 A1 Feb. 23, 2012

(30) Foreign Application Priority Data

Aug. 18, 2010 (DE) .......................... 10 2010 037 026

(51) Int. Cl.
*A61B 18/02* (2006.01)
*A61M 39/10* (2006.01)

(52) U.S. Cl.
CPC ............ *A61B 18/02* (2013.01); *A61M 39/10* (2013.01); *A61B 2018/0262* (2013.01); *A61M 39/105* (2013.01); *Y10T 16/466* (2015.01)

(58) Field of Classification Search
CPC ..... A61M 39/10; A61M 39/105; A61B 18/02; A61B 2018/0262
USPC ....................................... 606/20–26
See application file for complete search history.

(56) References Cited

U.S. PATENT DOCUMENTS

| 3,272,203 | A |   | 9/1966  | Chato |
|-----------|---|---|---------|-------|
| 3,439,680 | A | * | 4/1969  | Thomas, Jr. ........... A61B 18/02 219/241 |
| 3,536,075 | A | * | 10/1970 | Thomas, Jr. ................... 606/23 |
| 3,993,075 | A | * | 11/1976 | Lisenbee et al. ............... 606/25 |
| 4,377,168 | A |   | 3/1983  | Rzasa et al. |
| 5,573,532 | A | * | 11/1996 | Chang et al. .................. 606/26 |
| 5,910,104 | A | * | 6/1999  | Dobak et al. ................. 600/121 |

(Continued)

FOREIGN PATENT DOCUMENTS

CN 101188977 A 5/2008
DE 697 29 643 T2 7/2005

(Continued)

*Primary Examiner* — Eun Hwa Kim
(74) *Attorney, Agent, or Firm* — Blank Rome LLP (57) ABSTRACT

A device for the fluid-conveying connection of at least one application probe. The device comprising at least two coaxially extending application line elements, with a supply tubing set, said tubing set comprising at least two parallel-extending supply line elements, in a grip element of a surgical instrument such as a cryosurgical instrument, such that, in a connected state, each supply line element is in fluid communication with at least one associated application line element. A fluid-diverting element is provided and arranged, or can be arranged, in the grip element in fluid communication with an application line connecting region for the connection of the application line elements and with a supply line connecting region for the connection of the supply line elements. At least two transfer line elements designed as an integral part of the fluid-diverting element are in fluid communication with the application line connecting region via the application line connecting region.

22 Claims, 3 Drawing Sheets

(56) References Cited

U.S. PATENT DOCUMENTS

| | | | |
|---|---|---|---|
| 6,270,493 B1 * | 8/2001 | Lalonde | A61B 18/02 606/23 |
| 2005/0038422 A1 | 2/2005 | Maurice | |
| 2005/0081541 A1 * | 4/2005 | Copping | A61B 18/02 62/177 |
| 2007/0250050 A1 * | 10/2007 | Lafontaine | 606/21 |
| 2009/0163902 A1 | 6/2009 | DeLonzor et al. | |

FOREIGN PATENT DOCUMENTS

| | | | | |
|---|---|---|---|---|
| GB | 1 111 757 | 5/1968 | | |
| WO | WO 2009/090647 A2 | 7/2009 | | |
| WO | WO 2009090647 A2 * | 7/2009 | | A61B 18/02 |

* cited by examiner

DEVICE FOR THE FLUID-CONVEYING CONNECTION OF AT LEAST ONE APPLICATION PROBE WITH A SUPPLY TUBING SET, AND HANDLE FOR A SURGICAL INSTRUMENT

FIELD OF THE INVENTION

Embodiments of the invention relate to a device for the fluid-conveying connection of at least one application probe, said device comprising at least two coaxially extending application line elements, and a supply tubing set, said tubing set comprising at least two parallel-extending supply line elements, in a grip element of a surgical instrument, such as a cryosurgical instrument, such that, in a connected state, each supply line element is in fluid communication with at least one associated application line element.

In addition, embodiments of the invention relate to a handle for a surgical instrument, such as a cryogenic surgical instrument, comprising a grip element, a supply tubing set with at least two parallel-extending supply line elements and at least one application probe with at least two coaxially extending application line elements, in which each supply line element can be connected, or is connected, with an associated application line element in the grip element.

BACKGROUND

Such handles and connecting devices inside such handles are known in the art. In most cases, a supply tubing set and an application probe are attached to the handles, said application probe being supplied with an application fluid via the supply tubing set. The mentioned connecting devices are disposed for the fluid-conveying connection of the tubing set with the application probe to supply an application fluid to the application probe via the tubing set and the supply line elements provided therein, and to remove said application fluid from said application probe. To accomplish this, the fluid is delivered to the grip element via at least one supply line element and from said grip element to the application probe, where said fluid flows to the application probe head via an application line element extending on the outside circumference of the application probe. From there, said fluid is returned through a coaxial internal application line element and conveyed into a return supply line element through which said fluid flows back to the supply unit.

The connection between parallel supply line elements or the supply tubing set and the coaxial application line elements or the application probe is an essential aspect of the aforementioned devices.

A large number of devices for connecting or rerouting parallel and coaxial lines are known in the art, all of said devices having a highly complex and, most of all, sensitive and very bulky design.

According to experts, there is a need for handles, and thus also the need for connecting devices, that enable the interchangeable attachment of application probes. This is understood to mean that the handles or surgical instruments can be used, for example, not only as "normal" cryosurgical instruments, but also as defreeze devices, wherein the inflow of the still warm fluid takes place on the outside and the return flow of the cooled fluid takes place on the inside. Considering this "reverse" application, the operation of the application probe with the fluid in reverse flow direction must be possible.

Due to the extremely high costs in the surgical instruments' field, there has been a move toward modular instruments that use a minimal variety of components; there is a need for handles or surgical instruments that enable, in a simple manner, the attachment of different application probes to the handle, without requiring expensive structural modifications of the device.

This object has only been inadequately achieved by the prior art.

SUMMARY

Consequently, it is the object of the embodiments of the invention to offer a surgical instrument or devices of the aforementioned type that are suitable for said surgical instrument, said devices providing a simple, cost-favorable and reliable connection of at least one, but preferably more than one, different application probe with a supply tubing set.

In particular, the objects are achieved by:

A device for the fluid-conveying connection of at least one application probe, said device comprising at least two coaxially extending application line elements, and a supply tubing set, said tubing set comprising at least two parallel-extending supply line elements, in a grip element of a surgical instrument such as a cryosurgical instrument, such that, in a connected state, each supply line element is in fluid communication with at least one associated application line element. A fluid-diverting element is provided and arranged, or can be arranged, in the grip element in fluid communication with an application line connecting region for the connection of the application line elements and with a supply line connecting region for the connection of the supply line elements; at least two transfer line elements designed as an integral part of the fluid-diverting element are in fluid communication with the application line connecting region via the application line connecting region.

The object is also achieved by a handle for a surgical device comprising a grip element, a supply tubing set, at least two parallel-extending supply line elements and at least one application probe comprising at least two coaxially extending application line elements. Each supply line element can be connected, or is connected, with an associated application line element in the grip element. A device for the fluid-conveying connection of the at least one application probe is provided on the supply tubing set in accordance with the aforementioned or hereinafter specified type.

An essential aspect of the embodiments is that a fluid-diverting element is provided in the grip element, whereby the fluid-diverting element features connecting regions for the application line elements and the supply line elements, and establishes the fluid communication for these line elements via transfer elements that are an integral part of the fluid-diverting element.

Consequently, it is possible to attach, for example, a supply tubing set comprising two or more supply line elements to the grip element or to a fluid-diverting element arranged therein; the respective supply line elements can be brought into fluid communication in a very simple, space-saving and cost-favorable manner, via the integral transfer elements, with an application probe provided in an application line connecting region, whereby the conveying delay between the parallel-extending supply line elements and the coaxially extending application line elements has been resolved in a reliable and space-saving manner.

Preferably, the fluid-diverting element is an element configured as a one-piece turned part, milled part, or the like. In this situation, a one-piece configuration is understood to mean that at least corresponding receptacle regions for the application line connecting region, the supply line connecting region and the previously described transition elements are provided in one piece in the fluid-diverting element. In doing so, it is possible, for example, to configure appropriate receptacle regions on the fluid-diverting element, in which case appropriate sealing elements may be interposed for the fluid-tight connection of the respective supply line or application line elements.

Preferably, the transfer line elements in the interior of the fluid-diverting element are fabricated to act as guides produced by milling, casting, or the like.

Preferably, the fluid-diverting element is configured, at least in part, as a cylindrical element or as a similarly elongated volume body. It is a compact design that allows the simple and safe mounting of a surgical instrument in a grip element.

Preferably, the supply line connecting region and/or the application line connecting region are arranged on the faces or similar oppositely arranged sides of the cylindrical element or similarly elongated volume body. In this manner, it is possible to integrate the fluid-diverting element in the preferably elongated grip elements of surgical instruments in a very simple manner.

Preferably, the supply line connecting region and/or the application connecting region are arranged in a receptacle region that is an integral part of the fluid-diverting element such that they do not project beyond the exterior geometric configuration of the fluid diverter. As has been previously mentioned, the receptacle region(s) form suitable free spaces for the respective connecting regions on the fluid-diverting element to accommodate the respective line elements; under certain circumstances, however, the receptacle region(s) may also accommodate the tubing set or the application probe at least partially in the fluid-diverting element, whereby the sealing elements, clamping elements, or similar elements required for the fluid-tight connection of the respective elements are preferably fully accommodated in the respective receptacle regions.

Preferably, the fluid-diverting element and, in particular, the application line connecting region comprise an application probe receptacle region, such that it enables the releasable attachment of the application probe on the fluid-diverting element. Thus, the application probe receptacle region is preferably configured such that a complementary application probe molded part of the application probe comes into operative connection with the application probe receptacle region such that the probe is properly position, preferably on the device or on an adjacent grip element or similar element and is connected in a fluid-tight manner in the application line connecting region. Thus, the application probe receptacle region may be, for example, a receptacle region that is coaxial relative to the application line connecting region, into which an appropriately configured application probe molded part of the application probe can be inserted, in which case, in the inserted position, the application line elements come into fluid communication with the transfer elements and, at the same time, the application probe is fixed in position on the fluid diverter and/or on the associate grip element or similar element.

The advantage of such an embodiment is that it is possible, in a very simple manner, to connect the application probe with the supply tubing set, whereby it is also possible to connect a plurality of differently configured application probes having identically configured application probe molded parts for the connection with the tubing set in the application connecting region or in the application probe receptacle region.

Preferably, in doing so, the application probe receptacle region is an integral part of the fluid-diverting element such that mechanical loads acting on the application probe can be removed via the fluid-diverting element and output by said fluid-diverting element into the grip element.

Preferably, the application probe receptacle region comprises at least one locking means by which the application probe can be detachably locked in place—without tools—on the fluid-diverting element and/or on an associate handle or on a similar element. Such a locking means may be, for example, a bayonet joint element by which the application probe can be locked in place in the application probe receptacle region. In this situation, any locking means known in the art can be used and, in particular, such locking means can be used that enable the tool-less and thus very rapid locking and unlocking of the application probe.

Preferably, the supply line connecting region for each supply line element that is to be connected has a complementary supply line connecting element, by which the respective supply line element can be connected with the corresponding transfer element in a fluid-tight manner, wherein the supply line connecting elements and/or the supply line elements are configured complementary to each other such that each supply line element can be selectively connected with each supply line connecting element. In this way, it is possible to change the line arrangement within the grip element such that, for example, an instrument used in cryosurgery can also be used as a defreeze instrument. If, in a first treatment case (i.e., "defreeze probe") an application fluid is delivered via the parallel-extending supply line elements to the application probe such that the (still warm) application fluid is conveyed to the application probe head in the application line element located outside the application probe and is returned (cooled) on the inside, it is possible—due to a corresponding change of the fluid direction between the supply line connecting elements and the supply line elements, or by a corresponding change in the connecting region of the supply unit—to achieve fluid flow in the opposite direction, whereby the (still warm) application fluid is moved forward to the application probe head in the application line element arranged on the inside and returned (cooled) in the coaxial application line element arranged on the outside. Such a switch in fluid direction can be achieved with the use of an appropriately configured reversing element that is provided in the tubing set or also in the fluid-diverting element.

Preferably, a filter accommodating space is integrated in the fluid-diverting element for the accommodation of a filter element such that the filter element is arranged inside at least one fluid path between a supply line element and an application line element. In this manner, it is possible, for example, to arrange a filter inside a line element used as an inflow to prevent a potential blockage of the downstream application probe head and its mostly much thinner line elements. Preferably, the accommodation space is configured such that it allows the insertion of the filter or also several filters—even with the previously described reverse flow direction—so that the filter element may be arranged in the inflow element as well as in the return flow element that, after "diversion", is also an inflow element.

As mentioned above, the embodiments of the invention also relate to a surgical instrument of the aforementioned type, said instrument comprising the connecting device discussed above. It should be appreciated that each and every specification of this device is also applicable to such a handle, with the explicit separate identification being omitted to avoid being redundant.

Additional embodiments of the invention can be inferred from the dependent claims.

BRIEF DESCRIPTION OF THE DRAWINGS

Embodiments of the invention will be described in greater detail with reference to the drawings, in which.

DETAILED DESCRIPTION

Hereinafter, the same reference numbers are used for the same parts and parts acting in the same manner, whereby, in some instances, a prime is also used.

Figure 1:
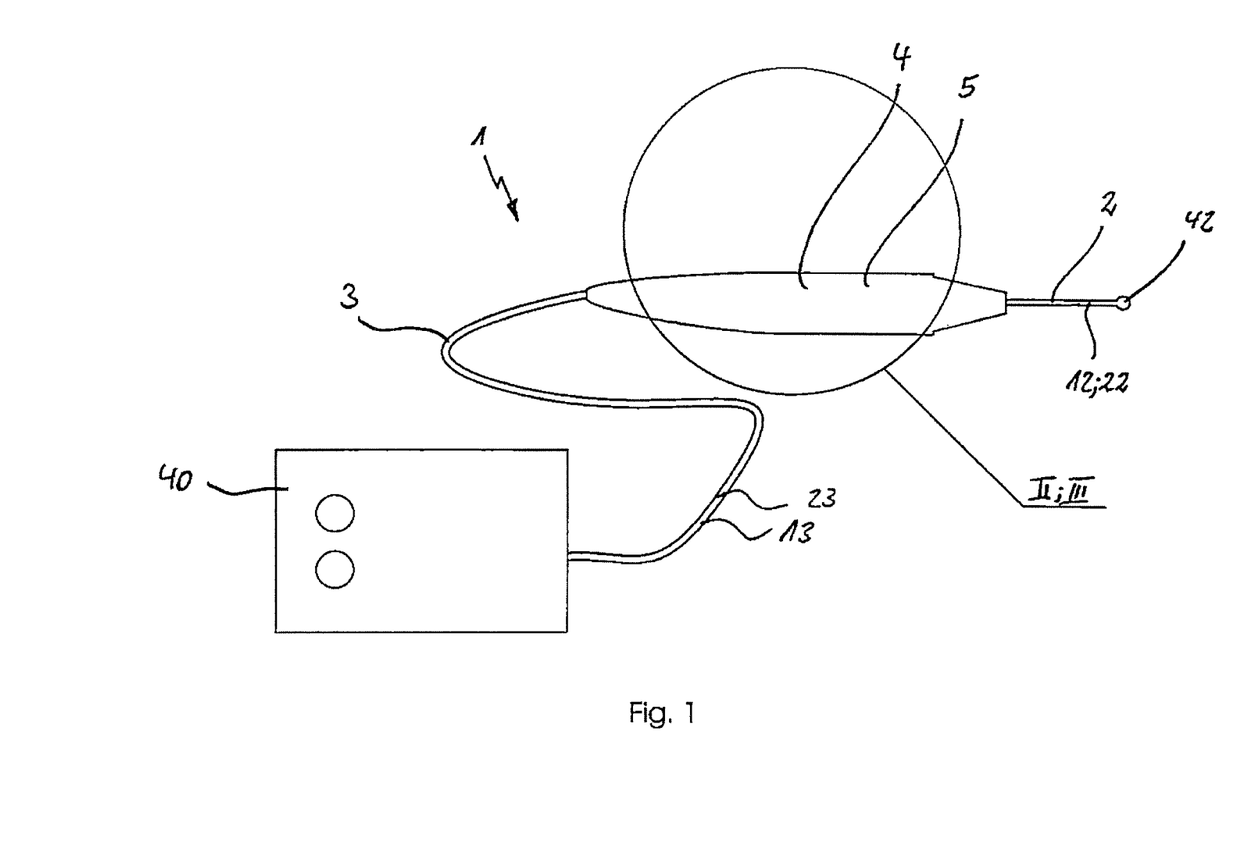
FIG. 1 is a schematic representation of an embodiment of a surgical device, in particular, a cryosurgical device.

FIG. 1 shows an embodiment of a surgical instrument 1 such as those used, for example, in cryosurgery.

Shown is a supply unit 40 that supplies a handle 5 with an application fluid via a supply tubing set 3. The illustrated tubing set 3 comprises two supply line elements 13, 23, one of which is used as a feeding supply line element 13 and the other is used as the discharging supply line element 23, to deliver the application fluid from the supply unit 40 to the handle 5 and to discharge said fluid therefrom.

The handle 5, in turn, comprises a grip element 4 that is disposed to accommodate the tubing set 3 and the supply line elements 13, 23, and comprises an application probe 2 that, in the illustrated embodiment, is configured as a cryosurgical probe with a coaxial line arrangement and coaxially extending application line elements 12, 22.

Considering the surgical instrument shown in FIG. 1, as will be described in detail below, an application fluid is supplied to the grip element 4 via the supply unit 40 and the feeding supply line element 13 of the tubing set 3 and delivered, from said grip element—depending on the diverter status and the connected application probe 2—to an application probe head 42 via application line element 12 and returned to the grip element 4 via associated return-flow application line element 22, and conveyed from there to the supply unit 40 via the discharging supply line element 23.

Figure 2:
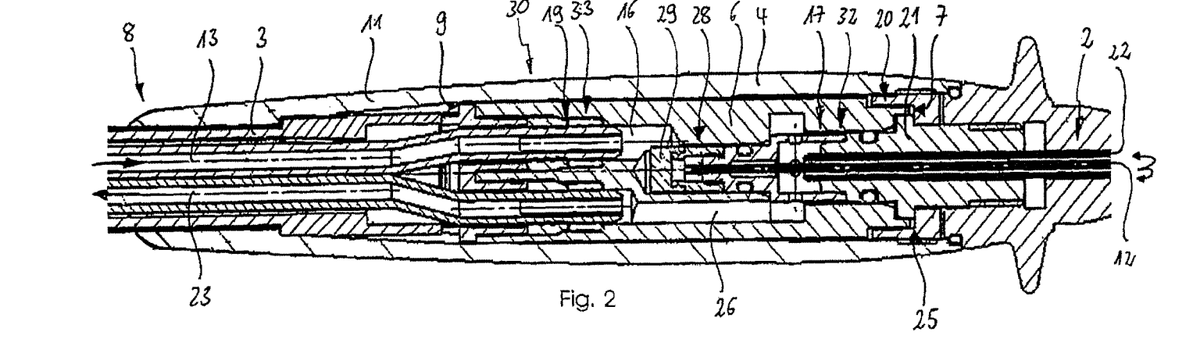
FIGS. 2 and 3 are cross-sections through two embodiments of a grip element of the surgical device in accordance with FIG. 1.
Figure 4:
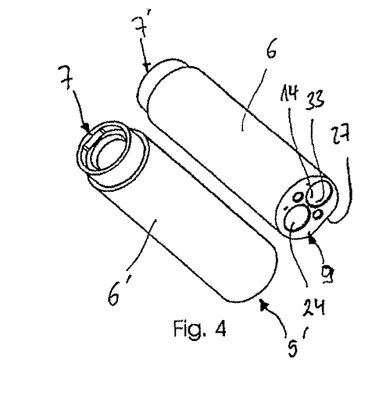
FIG. 4 illustrates two isometric representations of a fluid diverter as has been built into the grip element in accordance with FIGS. 2 and 3.

As shown by FIGS. 2 and 4, the connection of the supply line elements 13, 23 with the application line elements 12, 22 is accomplished via a connecting device 30 comprising, as an essential component, a fluid-diverting element 6 that is arranged or can be arranged in the grip element 4, which comprises an application line connecting region 32 for the connection of the application line elements 12, 22, and comprises a supply line connecting region 33 for the connection of the supply line elements 13, 23. In addition, the fluid-diverting element 6 comprises at least two transfer line elements 16, 26, being an integral part of the fluid-diverting element 6, by which the application line connecting region 32 is in fluid communication with the supply line connecting region 33 or the respective application line or supply line elements 12, 22; 13, 23 located there.

As such, the fluid-diverting element 6 is configured as a stand-alone component so that the supply line elements 13, 23 and the application line elements 12, 22 can be brought into fluid communication so as to be space-saving and securely connected to said component.

Figure 3:
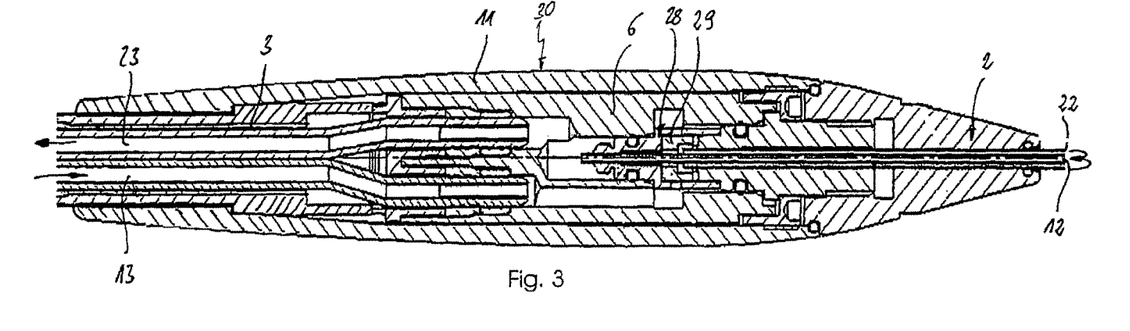

FIGS. 2 and 3 show details of two embodiments of a grip element 4 of the surgical instrument 1 shown in FIG. 1; the two embodiments essentially differ due to a "reversal" of the supply line elements 13, 23 used for inflow and outflow.

FIG. 2 shows a grip element 4 comprising, on its proximal end 8, the supply tubing set 3 with its two supply line elements 13, 23. In this embodiment, the supply line element 13 is used for the supply of an application fluid, whereas the supply line element 23 is used for discharge. The two supply line elements 13, 23 are connected with the application probe 2 or the application line elements 12, 22 of the latter via the fluid-diverting element 6 such that the application fluid is introduced into the inner application line element 12 and conveyed from there to the application probe head 42 (see FIG. 1), expanded there and, in doing so, cooled, and introduced into the coaxially outer application line element 22, flowing back therein and leaving the grip element 4 via the supply line element 23.

The line elements 12, 13 and 23, 22, respectively, are connected via the fluid-diverting element 6 in accordance with the embodiment of the invention, said fluid-diverting element being configured, in this case, as an essentially cylindrical element (see FIGS. 4 through 9 also). On both of its faces 7, 9, the fluid-diverting element 6 has connecting regions, namely the application line connecting region 32 for the connection of the application line elements 12, 22 and the supply line connecting region 33 for the connection of the supply line elements 13, 23. As such, in accordance with the embodiment of the invention, the supply line connecting region 33 is connected with the application line connecting region 32 via the transfer line elements 16, 26 integrated in the fluid-diverting element 6 so that the supplied application fluid can be transported to the application probe 2 and away from said application probe.

A filter accommodating space 28 is provided in the fluid path between the feeding supply line element 13 and the coaxially internal application line element 12; a filter element 29 is arranged or can be arranged in the fluid path between the two line elements 12, 13 in the filter accommodating space. This filter element 29 filters out contaminants that are potentially contained in the supplied application fluid and prevents a blockage of the extremely thin application lines 12, 22. As will still be described in detail below, the filter accommodating space 28 has a configuration such that it enables not only the arrangement of the filter element 29 in the supply region, but also in the discharge region, i.e., in the fluid path between the application line element 22 and the feeding supply line element 13 (see FIG. 3). If, as is shown specifically in FIG. 3, the filter element 29 is integrated there, it is possible to operate the surgical instrument 1 in "reverse mode", i.e., for example, in defreeze mode, wherein the supply and discharge of the application fluid are reversed.

Considering this embodiment, the application and supply line connecting regions 32, 33 are embodied such that they each possess a receptacle region 17 or 19, said receptacle region being configured and arranged in the fluid-diverting element 6 so that the supply line connecting region or the application line region 32 do not project beyond the outside geometric configuration of the fluid-diverting element 6. This means that the respective supply and discharge line elements 12, 13; 22, 23 are connected in a fluid-tight manner with the fluid diverter 6 inside the integral receptacle regions 17, 29 and are thus in fluid-communicating connection with each other.

An outside coat 11 is directly molded to the essentially cylindrical fluid-diverting element 6, resulting in a very simple and cost-favorable surgical instrument that is extremely resistant to wear.

The one-piece fluid-diverting element 6 additionally comprises, on its one face end 7, an application probe receptacle region 20 via which the application probe 2—together with the application line elements 12, 22—can be fastened and locked to the fluid-diverting element 6 or the grip element 4. To accomplish this, the application probe 2 comprises a receptacle molded part 21 that is shaped to be complementary to the application line connecting region 32 such that the application probe 2 can be fastened to the grip element 4 or the fluid-diverting element 6 in a simple manner and, most importantly, without the use of tools. To accomplish this, a locking means 25 is provided on the receptacle molded part 21, said locking means being used to detachably hold the application probe 2 in place on the fluid-diverting element 6 or the grip element 4. It should be noted that any locking means known in the art can be used such as, for example, bayonet joints or catch elements.

Consequently, the illustrated embodiment advantageously allows the grip element 4 to be provided with different application probes 2 that can be exchanged in a simple and, most importantly, rapid manner.

As mentioned above, FIG. 3 shows an embodiment that is similar to FIG. 2, wherein a "reversed" line direction of the supply line elements 13, 23 is provided. In contrast with the previously described grip element, in the embodiment in accordance with FIG. 3, the application fluid is supplied to the coaxially outer application line element 22 via (another) feeding supply element 14, delivered to the application probe head 42 (see FIG. 1), returned via the coaxially inner application line element 12 and discharged via the discharging supply line element 23. To prevent a blockage of the application probe 2 with this line arrangement employed by the so-called defreeze technique, a filter element 29 is provided in accordance with the embodiment of the invention at another feeding fluid connection between the supply line element 14 and the application line element 22. Other than that, the embodiment shown in FIG. 3 corresponds to the embodiment of FIG. 2.

Figures 5, 6:
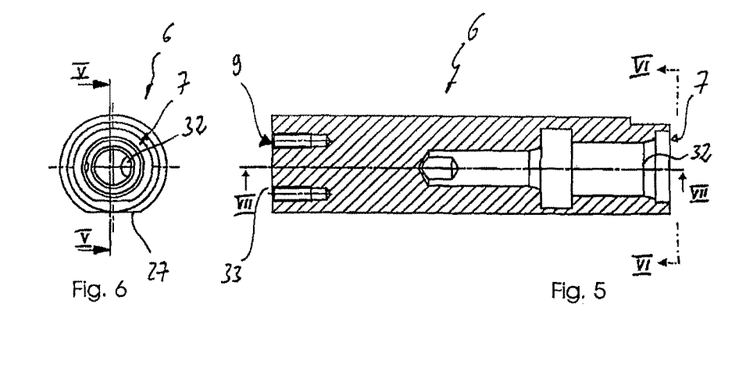
FIG. 5 illustrates a longitudinal section through the fluid diverter in accordance with FIG. 4, along the section line of FIG. 6.
FIG. 6 illustrates a view of the fluid diverter along the line of sight of FIG. 8.
Figures 7, 8:
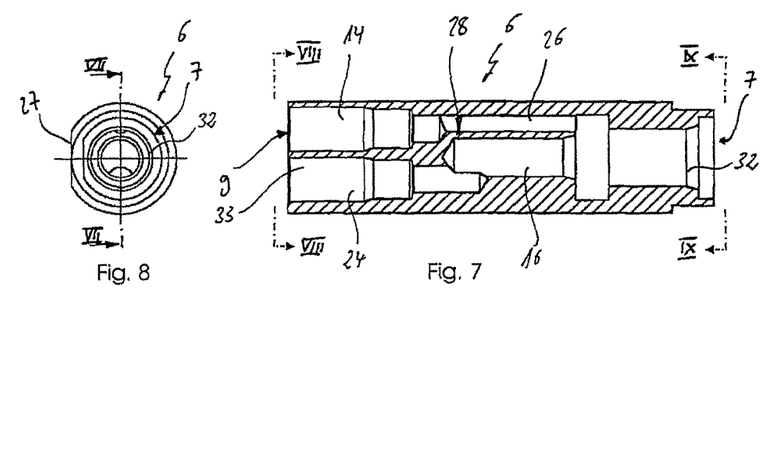
FIG. 7 illustrates a longitudinal section through the fluid diverter in accordance with FIG. 4, along the section line of FIG. 8.
FIGS. 8 and 9 are views of the fluid diverter, along the section line of FIG. 7.
Figure 9:
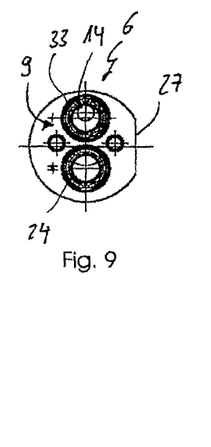

FIGS. 4 through 9 illustrate a perspective representation (FIG. 4) or longitudinal sections (FIGS. 5 and 7) of the above-described fluid diverter 6, as well as lateral face views (FIGS. 6, 8, 9). It can be seen that, in this embodiment, the fluid diverter 6 is configured as an essentially cylindrical component that has a flat area 27 in a section of its generated surface, said flat area providing a grip region on the finished grip element 4 (see, in particular, FIGS. 3 and 4) for a surgeon, on the one hand, and forming a reliable fixation of the fluid-diverting element 6 inside the outer coat 11 (see FIGS. 2 and 3), on the other hand.

On its one face 7, the fluid-diverting element 6 has the application line connecting region 32 that is disposed to act as the receptacle for the application probe 2 and the application lines 13, 23 formed therein (see FIGS. 2 and 3).

On its other face 9, the fluid-diverting element 6 has the supply line connecting region 33 that is disposed to act as the connection for the two supply line elements 13, 23 of the tubing set 3 (see FIGS. 2 and 3).

Each supply line connecting region 33 for each supply line element 13, 23 to be connected has a complementary supply line connecting element 14, 24 by which the respective supply line element 13, 23 (see FIGS. 2 and 3) can be connected in a fluid-tight manner with the corresponding transfer element 16, 26 (see, in particular, FIG. 7); in this embodiment, the supply line connecting elements 14, 24 and the supply line elements 13, 23 are configured complementary to each other such that each supply line element 13, 23 can be selectively connected with each supply line connecting element 14, 24.

In addition, considering the illustrated embodiment, it is possible to operate the grip element in accordance with the embodiments of the invention using different "loading directions" because it is possible, via the filter accommodating region 28, to arrange the filter element 29 (see FIGS. 2 and 3) such that the filter element is arranged in the feeding line system at all times. In this manner, a cryosurgical device in accordance with the embodiments of FIGS. 2 and 3 can be operated either in "normal" cryosurgery mode or in "defreeze" mode because it is possible to use the supply line element 13 (or 23) as either a supply element or a discharge element.

The invention claimed is:

1. A device for a fluid-conveying connection of at least one application probe to a handle of a cryoablation instrument, said device comprising:
   a supply tubing set, said tubing set comprising two parallel-extending flexible supply tubes; and
   a fluid-diverting element configured as a stand-alone, one-piece cylindrical element or an elongated volume body and arranged in a grip element of the handle, the fluid diverting element having a distal end, and proximal end an intermediate portion between the distal and proximal ends, and comprising:
      in the proximal end, a supply tube connecting region comprising, at least two supply tube connecting elements configured as parallel-extending voids in the proximal end of the fluid-diverting element, each of the at least two supply tube connecting elements configured to receive a distal portion of the two parallel-extending flexible supply tubes;
      in the distal end, a radially central positioned, with respect to the grip element, application line connecting region forming a seat to releasably receive and connect at least two coaxially extending application line elements of the at least one application probe; and
      in the intermediate portion, at least two transfer line elements configured as voids in the fluid-diverting element and through which the application line connecting region is in fluid communication with the supply tube connecting region such that at least one of the two supply tube connecting elements are positioned radially offset from the corresponding one of the at least two transfer line elements,
   wherein the two parallel-extending supply line tubes extend into the proximal end of the fluid-diverting element when connected to the supply tube connecting region,
   wherein each of the at least two transfer line elements and the at least two supply tube connecting elements are positioned apart from, in a coaxial direction, a radial center of the fluid-diverting element, wherein the application line connecting region is adapted to receive a receptacle molded part such that the at least one application probe can be fastened to the fluid diverting element, wherein the two parallel-extending supply line tubes are positioned radially offset from the corresponding at least two coaxially extending application line elements.

2. The device of claim 1, wherein the fluid-diverting element is configured as a one-piece turned part.

3. The device of claim 1, wherein the fluid-diverting element is configured as a one-piece milled part.

4. The device of claim 1, wherein the supply tube connecting region and/or the application line connecting region are arranged on faces of the cylindrical element.

5. The device of claim 1, wherein the supply tube connecting region and/or the application line connecting region are arranged on oppositely arranged sides of the cylindrical element.

6. The device of claim 1, wherein the supply tube connecting region and/or the application line connecting region are arranged on faces of the elongated volume body.

7. The device of claim 1, wherein the supply tube connecting region and/or the application line connecting region are arranged on oppositely arranged sides of the elongated volume body.

8. The device of claim 1, wherein the supply tube connecting region and/or the application line connecting region are arranged in a receptacle region that is an integral part of the fluid-diverting element such that they do not project beyond the exterior geometric configuration of the fluid-diverting element.

9. The device of claim 1, wherein the fluid-diverting element and the application line connecting region comprise an application probe receptacle region such that they enable a releasable attachment of the at least one application probe on the fluid-diverting element.

10. The device of claim 9, wherein the application probe receptacle region comprises at least one locking means by which the at least one application probe can be detachably locked in place on the fluid-diverting element.

11. The device of claim 1, wherein each of the respective at least two supply tube connecting elements is configured to connect a respective one of the two parallel-extending supply line tubes with a corresponding one of the at least two transfer elements in a fluid-tight manner, wherein the complementary supply tube connecting elements and/or the two parallel-extending supply line tubes are configured complementary to each other such that each of the two parallel-extending supply line tubes can be selectively connected with each supply tube connecting element.

12. The device of claim 1, wherein none of the two parallel-extending supply line tubes is coaxial to the grip element.

13. A handle for a cryoablation instrument, said handle comprising:
    a grip element;
    a supply tubing set with two parallel-extending flexible supply tubes; and
    a device for a fluid-conveying connection of at least one application probe having at least two coaxially extending application line elements and a receptacle molded part with the supply tubing set, said device comprising:
        a fluid-diverting element configured as a stand-alone, one-piece cylindrical element or an elongated volume body and arranged in the grip element of the handle, the fluid diverting element having a distal end, and proximal end an intermediate portion between the distal and proximal ends, and comprising:
            in the proximal end, a supply tube connecting region comprising at least two supply tube connecting elements configured as parallel-extending voids in the proximal end of the fluid-diverting element, each of the at least two supply tube connecting elements configured to receive a distal portion of the two parallel-extending flexible supply tubes;
            in the distal end, a radially central positioned, with respect to the grip element, application line connecting region forming a seat to releasably receive and connect the at least two coaxially extending application line elements of the at least one application probe; and
            in the intermediate portion, at least two transfer line elements configured as voids in the fluid-diverting element and through which the application line connecting region is in fluid communication with the supply tube connecting region such that at least one of the two supply tube connecting elements are positioned radially offset from the corresponding one of the at least two transfer line elements,
    wherein the two parallel-extending supply line tubes extend into the proximal end of the fluid-diverting element when connected to the supply tube connecting region,
    wherein each of the at least two transfer line elements and the at least two supply tube connecting elements are positioned apart from, in a coaxial direction, a radial center of the fluid-diverting element,
    wherein the application line connecting region is adapted to receive the receptacle molded part such that the at least one application probe can be fastened to the fluid diverting element, and
    wherein the two parallel-extending supply line tubes are positioned coaxially apart from the corresponding at least two coaxially extending application line elements.

14. The handle of claim 13, wherein the surgical instrument is a cryosurgical instrument.

15. The handle of claim 13, wherein, the fluid-diverting element is configured as a one-piece turned part or a one-piece milled part.

16. The handle of claim 13, wherein the supply tube connecting region and/or the application line connecting region are arranged on faces of the cylindrical element or elongated volume body.

17. The handle of claim 13, wherein the supply tube connecting region and/or the application line connecting region are arranged on oppositely arranged sides of the cylindrical element or elongated volume body.

18. The handle of claim 13, wherein the supply tube connecting region and/or the application line connecting region are arranged in a receptacle region that is an integral part of the fluid-diverting element such that they do not project beyond the exterior geometric configuration of the fluid-diverting element.

19. The handle of claim 13, wherein the fluid-diverting element and the application line connecting region comprise an application probe receptacle region such that they enable a releasable attachment of the at least one application probe on the fluid-diverting element.

20. The handle of claim 19, wherein the application probe receptacle region comprises at least one locking means by which the at least one application probe can be detachably locked in place on the fluid-diverting element.

21. The handle of claim 13, wherein each of the respective at least two supply tube connecting elements is configured to connect a respective one of the two parallel-extending supply line tubes with a corresponding one of the at least two transfer elements in a fluid-tight manner, wherein the complementary supply tube connecting elements and/or the two parallel-extending supply line tubes are configured complementary to each other such that each one of the two parallel-extending supply line tubes can be selectively connected with each supply tube connecting element.

22. The handle of claim 13, wherein none of the two parallel-extending supply line tubes is coaxial to the grip element.

* * * * *